(12) United States Patent
Dietz et al.

(10) Patent No.: US 9,170,246 B2
(45) Date of Patent: Oct. 27, 2015

(54) FLUID STORAGE AND DISPENSING SYSTEM INCLUDING DYNAMIC FLUID MONITORING OF FLUID STORAGE AND DISPENSING VESSEL

(71) Applicant: Entegris, Inc., Billerica, MA (US)

(72) Inventors: James Dietz, Allison Park, PA (US); Steven E. Bishop, Corrales, NM (US); James V. McManus, Bethel, CT (US); Steven M. Lurcott, Deerfield Beach, FL (US); Michael J. Wodjenski, New Milford, CT (US); Robert Kaim, Brookline, MA (US); Frank DiMeo, Jr., Falls Church, VA (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 14/054,497

(22) Filed: Oct. 15, 2013

(65) Prior Publication Data

US 2014/0041440 A1 Feb. 13, 2014

Related U.S. Application Data

(63) Continuation of application No. 13/171,434, filed on Jun. 28, 2011, now Pat. No. 8,555,705, which is a continuation of application No. 11/577,864, filed as application No. PCT/US2005/038173 on Oct. 24, 2005, now Pat. No. 7,966,879, which is a continuation-in-part of application No. 10/972,542, filed on Oct. 25, 2004, now Pat. No. 7,955,797.

(51) Int. Cl.
*G01D 1/00* (2006.01)
*G01N 33/00* (2006.01)
(Continued)

(52) U.S. Cl.
CPC ............ *G01N 33/00* (2013.01); *G01F 23/0076* (2013.01); *H01L 21/568* (2013.01);
(Continued)

(58) Field of Classification Search
CPC ...................... B01D 53/0047; B01D 2253/102; G01N 1/2035
See application file for complete search history.

(56) References Cited

U.S. PATENT DOCUMENTS

| 3,698,249 A | 10/1972 | Weaver |
| 4,257,260 A | 3/1981 | Beatson et al. |

(Continued)

FOREIGN PATENT DOCUMENTS

| KR | 2001-0036561 A | 5/2001 |
| KR | 2001-0051105 A | 6/2001 |

(Continued)

OTHER PUBLICATIONS

Hottinger Baldwin Messtechnik GmbH, "Strain Gages and Accessories", "Accessed via: http://www.hbm.com/data/softdoc/hbm/data/s1265.pdf", Jul. 18, 2006, pp. 1-100.

*Primary Examiner* — Zandra Smith
*Assistant Examiner* — Andre' C Stevenson
(74) *Attorney, Agent, or Firm* — Hultquist, PLLC; Steven H. Hultquist; Rosa Yaghmour

(57) ABSTRACT

A monitoring system for monitoring fluid in a fluid supply vessel during operation including dispensing of fluid from the fluid supply vessel. The monitoring system includes (i) one or more sensors for monitoring a characteristic of the fluid supply vessel or the fluid dispensed therefrom, (ii) a data acquisition module operatively coupled to the one or more sensors to receive monitoring data therefrom and responsively generate an output correlative to the characteristic monitored by the one or more sensors, and (iii) a processor and display operatively coupled with the data acquisition module and arranged to process the output from the data acquisition module and responsively output a graphical representation of fluid in the fluid supply vessel, billing documents, usage reports, and/or resupply requests.

17 Claims, 3 Drawing Sheets

(51) Int. Cl.
*H01L 23/538* (2006.01)
*H01L 23/00* (2006.01)
*H01L 21/683* (2006.01)
*H01L 25/03* (2006.01)
*H01L 25/16* (2006.01)
*H05K 1/18* (2006.01)
*G01F 23/00* (2006.01)
*H01L 21/56* (2006.01)
*H01L 25/065* (2006.01)
*H05K 3/46* (2006.01)

(52) U.S. Cl.
CPC ........ *H01L21/6835* (2013.01); *H01L 23/5389* (2013.01); *H01L 24/24* (2013.01); *H01L 24/82* (2013.01); *H01L 25/03* (2013.01); *H01L 25/16* (2013.01); *H05K 1/185* (2013.01); *H01L 21/561* (2013.01); *H01L 24/48* (2013.01); *H01L 25/0652* (2013.01); *H01L 2224/16225* (2013.01); *H01L 2224/16227* (2013.01); *H01L 2224/24011* (2013.01); *H01L 2224/2518* (2013.01); *H01L 2224/48091* (2013.01); *H01L 2224/48227* (2013.01); *H01L 2924/014* (2013.01); *H01L 2924/01005* (2013.01); *H01L 2924/01006* (2013.01); *H01L 2924/01013* (2013.01); *H01L 2924/01023* (2013.01); *H01L 2924/01027* (2013.01); *H01L 2924/01033* (2013.01); *H01L 2924/01058* (2013.01); *H01L 2924/01076* (2013.01); *H01L 2924/01078* (2013.01); *H01L 2924/01082* (2013.01); *H01L 2924/09701* (2013.01); *H01L 2924/14* (2013.01); *H01L 2924/19042* (2013.01); *H05K 3/4602* (2013.01); *H05K 2203/0165* (2013.01); *H05K 2203/085* (2013.01); *H05K 2203/1469* (2013.01)

(56) References Cited

U.S. PATENT DOCUMENTS

| | | | |
|---|---|---|---|
| 4,420,980 A | 12/1983 | Dunemann et al. | |
| 4,546,649 A | 10/1985 | Kantor | |
| 4,606,497 A | 8/1986 | Heimovics, Jr. | |
| 4,865,210 A | 9/1989 | Brainard, II | |
| 4,905,855 A | 3/1990 | Troiano et al. | |
| 5,146,098 A | 9/1992 | Stack | |
| 5,179,981 A | 1/1993 | Hicks et al. | |
| 5,383,352 A | 1/1995 | Krawetz et al. | |
| 5,413,159 A | 5/1995 | Olney et al. | |
| 5,493,903 A | 2/1996 | Allen | |
| 5,505,092 A | 4/1996 | Kowalski | |
| 5,518,528 A | 5/1996 | Tom et al. | |
| 5,597,085 A | 1/1997 | Rauworth et al. | |
| 5,704,965 A | 1/1998 | Tom et al. | |
| 5,704,967 A | 1/1998 | Tom et al. | |
| 5,707,424 A | 1/1998 | Tom et al. | |
| 5,882,384 A | 3/1999 | Tom et al. | |
| 5,883,305 A | 3/1999 | Jo et al. | |
| 6,019,823 A | 2/2000 | Tischler et al. | |
| 6,070,576 A | 6/2000 | Banucci et al. | |
| 6,073,759 A | 6/2000 | Lamborne et al. | |
| 6,079,252 A | 6/2000 | Tabler et al. | |
| 6,089,027 A | 7/2000 | Wang et al. | |
| 6,101,816 A | 8/2000 | Wang et al. | |
| 6,124,787 A | 9/2000 | Isakov et al. | |
| 6,132,492 A | 10/2000 | Hultquist et al. | |
| 6,156,578 A | 12/2000 | Tom | |
| 6,196,052 B1 | 3/2001 | May et al. | |
| 6,204,180 B1 | 3/2001 | Tom et al. | |
| 6,295,861 B1 | 10/2001 | Tom et al. | |
| 6,338,312 B2 | 1/2002 | Hayes et al. | |
| 6,343,476 B1 | 2/2002 | Wang et al. | |
| 6,360,546 B1* | 3/2002 | Wang et al. | 62/48.1 |
| 6,391,385 B1 | 5/2002 | Holst et al. | |
| 6,406,519 B1 | 6/2002 | Tom et al. | |
| 6,453,924 B1 | 9/2002 | Wang et al. | |
| 6,474,076 B2* | 11/2002 | Wang et al. | 62/48.1 |
| 6,478,547 B1 | 11/2002 | Savard et al. | |
| 6,494,343 B2 | 12/2002 | McManus et al. | |
| 6,500,238 B1 | 12/2002 | Brandes et al. | |
| 6,514,399 B1 | 2/2003 | Parce et al. | |
| 6,540,814 B2 | 4/2003 | Hayes et al. | |
| 6,540,819 B2 | 4/2003 | Tom et al. | |
| 6,561,213 B2 | 5/2003 | Wang et al. | |
| 6,581,623 B1 | 6/2003 | Carpenter et al. | |
| 6,592,653 B2 | 7/2003 | Wang et al. | |
| 6,660,063 B2 | 12/2003 | Tom et al. | |
| 6,716,271 B1 | 4/2004 | Arno et al. | |
| 6,742,993 B2 | 6/2004 | Savard et al. | |
| 6,749,671 B2 | 6/2004 | Holst et al. | |
| 6,805,728 B2 | 10/2004 | Sweeney et al. | |
| 6,843,830 B2 | 1/2005 | Sherer | |
| 6,939,394 B2 | 9/2005 | Carruthers | |
| 6,947,138 B2 | 9/2005 | Arno | |
| 6,955,198 B2* | 10/2005 | Wodjenski | 141/248 |
| 6,991,671 B2* | 1/2006 | Brestovansky et al. | 95/95 |
| 6,997,202 B2 | 2/2006 | Olander | |
| 7,018,448 B2 | 3/2006 | Wodjenski et al. | |
| 7,063,097 B2 | 6/2006 | Arno et al. | |
| 7,104,292 B2 | 9/2006 | Wodjenski | |
| 7,105,037 B2 | 9/2006 | Olander et al. | |
| 7,118,445 B2 | 10/2006 | Moore et al. | |
| 7,235,214 B2 | 6/2007 | Rodier et al. | |
| 7,275,420 B2 | 10/2007 | Discenzo | |
| 7,955,797 B2 | 6/2011 | McManus et al. | |
| 7,966,879 B2 | 6/2011 | Dietz et al. | |
| 2002/0103563 A1* | 8/2002 | Izawa et al. | 700/121 |
| 2002/0190283 A1 | 12/2002 | Seno et al. | |
| 2003/0029224 A1 | 2/2003 | Pratt et al. | |
| 2004/0251484 A1 | 12/2004 | Miyazaki et al. | |
| 2005/0008908 A1 | 1/2005 | Kaye et al. | |
| 2005/0255442 A1 | 11/2005 | Brassil et al. | |
| 2006/0091385 A1 | 5/2006 | Mair et al. | |
| 2006/0169033 A1* | 8/2006 | Discenzo | 73/64.56 |
| 2008/0017104 A1 | 1/2008 | Matyushkin et al. | |
| 2008/0191153 A1 | 8/2008 | Marganski et al. | |
| 2011/0232367 A1 | 9/2011 | McManus et al. | |
| 2011/0252883 A1 | 10/2011 | Dietz et al. | |

FOREIGN PATENT DOCUMENTS

| | | |
|---|---|---|
| KR | 2003-0092157 A | 12/2003 |
| WO | 2006101767 A2 | 9/2006 |

* cited by examiner

FLUID STORAGE AND DISPENSING SYSTEM INCLUDING DYNAMIC FLUID MONITORING OF FLUID STORAGE AND DISPENSING VESSEL

CROSS-REFERENCE TO RELATED APPLICATIONS

This is a continuation under 35 USC 120 of U.S. patent application Ser. No. 13/171,434 filed Jun. 28, 2011 in the names of James Dietz, et al. for "FLUID STORAGE AND DISPENSING SYSTEM INCLUDING DYNAMIC FLUID MONITORING OF FLUID STORAGE AND DISPENSING VESSEL," now U.S. Pat. No. 8,555,705, which is a continuation under 35 USC 120 of U.S. patent application Ser. No. 11/577,864 filed Apr. 24, 2007 in the names of James Dietz, et al. for "FLUID STORAGE AND DISPENSING SYSTEM INCLUDING DYNAMIC FLUID MONITORING OF FLUID STORAGE AND DISPENSING VESSEL," issued Jun. 28, 2011 as U.S. Pat. No. 7,966,879, which in turn is a national phase under the provisions of 35 USC 371 of International Patent Application PCT/US2005/038173 filed Oct. 24, 2005 and is a continuation-in-part under 35 USC 120 of U.S. patent application Ser. No. 10/972,542 filed Oct. 25, 2004 in the names of James V. McManus, James Dietz and Steven M. Lurcott for "FLUID STORAGE AND DISPENSING SYSTEM INCLUDING DYNAMIC FLUID MONITORING OF FLUID STORAGE AND DISPENSING VESSEL," and issued Jun. 7, 2011 as U.S. Pat. No. 7,955,797. The disclosures of said U.S. patent application Ser. No. 13/171,434, said U.S. patent application Ser. No. 11/577,864, said International Patent Application PCT/US 2005/038173 and said U.S. patent application Ser. No. 10/972,542 are hereby incorporated herein by reference in their respective entireties, for all purposes.

BACKGROUND

1. Field

The present invention relates to a fluid storage and dispensing system including dynamic monitoring of inventory of a fluid storage and dispensing vessel.

2. Description of the Related Art

In the field of semiconductor manufacturing, involving unit operations such as ion implantation, chemical vapor deposition, spin-on coating, etching, cleaning of process chambers, treatment of effluents, etc., it is common to utilize specialized fluid reagents of widely varying character.

Due to the high costs, significant toxicity, and ultra-high purity requirements of many of such fluid reagents, a variety of dedicated source vessels and containment apparatus have come into widespread usage in semiconductor manufacturing facilities. In many instances, these specialty fluid supply apparatus, which have replaced conventional gas cylinders in such service, are accessorized with various fluid monitoring and control devices. Such devices may for example include leak detection monitors, pressure transducers in dispensing lines, temperature sensors for ensuring that contained and dispensed fluid is at an appropriate thermal state for the associated process operation, mass flow controllers, restricted flow orifice elements, and the like.

Among the most innovative and commercially successful of the current generation of fluid storage and dispensing systems for semiconductor manufacturing reagents are those commercialized by ATMI, Inc. (Danbury, Conn.) under the trademarks SDS® and VAC®.

The SDS® fluid storage and dispensing system includes a vessel containing a solid-phase sorbent material having sorptive affinity for the semiconductor manufacturing fluid reagent, whereby fluid stored in the vessel on such sorbent material can be selectively desorbed therefrom and dispensed from the vessel under dispensing conditions. The semiconductor reagent fluid can be stored at low pressure as a result of its sorptive retention in the vessel, e.g., at subatmospheric pressures. As a result of such low pressure storage, a high level of safety is provided, in relation to high pressure gas cylinders in which a valve head failure can result in widespread dissemination of the fluid contents of the cylinder. The SDS® fluid storage and dispensing system is variously described in U.S. Pat. Nos. 5,518,528; 5,704,965; 5,704,967; and 5,707,424.

The VAC® fluid storage and dispensing system includes a vessel containing a semiconductor manufacturing fluid reagent and equipped with a pressure regulator that is interiorly disposed in the vessel and in flow communication with a dispensing assembly for dispensing of fluid at pressure determined by the set point of the pressure regulator. The pressure regulator set point can be set to a low dispensing pressure level. The VAC® fluid storage and dispensing system is variously described in U.S. Pat. Nos. 6,101,816; 6,089,027; 6,360,546; 6,474,076; and 6,343,476.

By its interior pressure regulator configuration, the VAC® fluid storage and dispensing system achieves an enhancement of safety in the containment of high pressure fluids, since the regulator prevents the discharge of fluid at pressure above the regulator set point, and since the regulator is inside the vessel and thereby protected from ambient contamination and direct impact.

In ion implant applications, the SDS® fluid storage and dispensing system has become a standard gas source in the semiconductor manufacturing industry. Currently, it is estimated that approximately 80% of the installed base of 4000 ion implant units worldwide utilize the SDS® fluid storage and dispensing system.

In order to assure proper utilization of the SDS® fluid storage and dispensing system, special consideration of the gas delivery system design including low pressure drop components and accurate measurement of sub-atmospheric (torr-level) pressure is required. This poses a particular problem in that there are a half dozen or so major manufacturers of ion implant equipment. Each manufacturer makes several model types and new products are released every 2-3 years. This circumstance results in a wide variety of ion implant systems and subsequently results in a myriad of gas monitoring techniques being in use, many of which are inadequate or otherwise inefficient and unstandardized.

In one of the most popular current ion implant system designs, gas monitoring of the inventory of fluid in the SDS® fluid storage and dispensing system requires navigating through a complex series of software files in order to determine pressure of the fluid in the SDS® fluid storage and dispensing vessel. The user then has to manually convert the pressure into a unit of fluid utilization. The problem with this approach is that the time required to navigate the software screens in this implementation is excessive, and most ion implant operators and technicians cannot understand the conversion mathematics required to convert the pressure reading into a meaningful utilization expression.

The foregoing deficiencies in monitoring utilization of fluid stored for dispensing in the fluid supply vessel is exacerbated by the fact that numerous implanter units, e.g., 5-20, are provided in a typically-sized semiconductor manufacturing facility, or "fab." The multiplicity of such units means that it often requires an operator or technician to spend hours in monitoring operations for all of the implanter units to determine the rate and extent of fluid consumption by the ion implanter, or other dispensed fluid-using equipment in the semiconductor fab.

Another problem with conventional approaches to monitoring fluid utilization for determining consumption of the fluid in the fluid supply vessel is that it is difficult to predict and alert fab personnel to the approaching end-point of the dispensing operation, when the vessel is nearly depleted of its fluid contents and approaching exhaustion.

Since existing approaches to determination of utilization are poor, it is a not infrequent occurrence that fab personnel run out of fluid without warning during active implant operation. This occurrence typically has a severe impact on fab productivity since the implant unit must then be shut down to accommodate change-out of the depleted fluid supply and dispensing vessel, and installation of a fresh vessel containing fluid for renewed operation. Since this occurrence is unscheduled, the efficiency with which the fluid storage and dispensing system can be replaced is less than if the event were scheduled or able to be predicted.

Another issue related to use of materials in semiconductor manufacturing relates to their cost. The prices of many specialty materials for semiconductor manufacturing are in a range of from $10-$200 US per gram and the packaging volumes of many specialty chemicals continues to increase due to higher consumption rates for larger wafer semiconductor process tools, e.g., 300 mm wafers and higher diameter wafers.

In consequence, consumers of specialty materials are often forced to purchase needed volumes of such materials at unit prices that often exceed their internally defined thresholds for capital purchases. Under Generally Accepted Accounting Principles in the United States (US GAAP), material purchases must be expensed at the time of purchase, so that purchasers expense the entire volume of purchased specialty chemical before using same in their material-utilizing processes. This is a significant operational cost burden on semiconductor manufacturing facilities.

There is therefore a significant need in the art for a fast, accurate and reliable approach to monitoring utilization and detecting end-point dispensing conditions in the use of fluid storage and dispensing systems of the above-described type.

There is concurrently a need for easing the operational cost burden on semiconductor manufacturing facilities deriving from the aforementioned accounting requirements of US GAAP for expensing entire volumes of purchased specialty chemicals for use in semiconductor manufacturing operations.

SUMMARY

The present invention relates generally to a system and method for dynamic monitoring of fluid in fluid storage and dispensing systems, such as those of the SDS®-type and the VAC®-type, to determine utilization of fluid in such systems.

In one aspect, the present invention relates to a monitoring system for monitoring fluid in a fluid supply vessel during operation including dispensing of fluid from the fluid supply vessel, said monitoring system including (i) one or more sensors for monitoring a characteristic of the fluid supply vessel or the fluid dispensed therefrom, (ii) a data acquisition module operatively coupled to the one or more sensors to receive monitoring data therefrom and responsively generate an output correlative to the characteristic monitored by the one or more sensors, and (iii) a processor and display operatively coupled with the data acquisition module and arranged to process the output from the data acquisition module and responsively output a visual representation such as a graph or audio signal, such as an alarm to denote the fluid in the fluid supply vessel.

In another aspect, the invention relates to a method of monitoring fluid in a fluid supply vessel during operation including dispensing of fluid from the fluid supply vessel, said method including (i) monitoring a characteristic of the fluid supply vessel or the fluid dispensed therefrom, (ii) acquiring data from said monitoring and responsively generating an output correlative to the monitoring characteristic, and (iii) processing the output from the data acquiring and responsively outputting a graphical representation of fluid in the fluid supply vessel.

Another aspect of the invention relates to a monitoring system for monitoring fluid in a fluid supply vessel during operation including dispensing of fluid from the fluid supply vessel, in which such monitoring system includes (i) one or more sensors for monitoring a characteristic of the fluid supply vessel or the fluid dispensed therefrom, (ii) a data acquisition apparatus operatively coupled to the one or more sensors to receive monitoring data therefrom and responsively generate an output correlative to the characteristic monitored by the one or more sensors, and (iii) a processor operatively coupled with the data acquisition apparatus and arranged to process the output from the data acquisition apparatus and responsively generate an output indicative of inventory of fluid in the fluid supply vessel.

A further aspect of the invention relates to a monitoring system for monitoring material usage during operation including dispensing of material, in which such monitoring system includes (i) one or more sensors for monitoring a characteristic of the dispensing, (ii) a data acquisition apparatus operatively coupled to the one or more sensors to receive monitoring data therefrom and responsively generate an output correlative to the characteristic monitored by the one or more sensors, and (iii) a processor operatively coupled with the data acquisition apparatus and arranged to process the output from the data acquisition apparatus and responsively generate an output indicative of inventory of material available for dispensing.

In another aspect, the invention relates to a semiconductor manufacturing facility, including: an ion implanter including a gas box holding a dopant source fluid supply; at least one sensor adapted to monitor at least one of temperature, pressure and flow rate of dopant source fluid dispensed from the dopant source fluid supply under dispensing conditions; a data acquisition module installed in the gas box and adapted to receive monitoring signals from the sensor; an output unit adapted to generate an output correlative to inventory of dopant source fluid in said dopant source fluid supply; and a communication connection between the data acquisition module and the output unit.

Yet another aspect of the invention relates to a system for determining consumption of dopant source fluid in an ion implanter supplied with dopant source fluid from a dopant source fluid supply in a gas box of the ion implanter, wherein said dopant source fluid supply includes a sorbent medium having sorptive affinity for the dopant source fluid, and from which adsorbed dopant source fluid is desorbed under dispensing conditions, in which the system includes:

a temperature sensor adapted to sense gas box temperature T;

a pressure monitor adapted for measuring the fluid storage and dispensing vessel pressure P;

the dopant source fluid supply including a dopant source fluid storage and dispensing vessel of a predetermined size containing a predetermined weight of said sorbent medium; and a monitoring and control system operatively coupled to said temperature sensor and said pressure monitor, and adapted to conduct the steps of:

setting an end-point pressure for dispensing dopant source fluid from the dopant source fluid storage and dispensing vessel;

determining temperature coefficients dP/dT at various pressures;

determining temperature coefficient for the end-point pressure;

normalizing measured pressure from the pressure monitor to a predetermined temperature;

normalizing the end-point pressure to the predetermined temperature;

determining isotherm equations at the predetermined temperature for the sorbent medium and dopant source fluid; and determining, using the isotherm equations, the amount of dopant source fluid remaining in the fluid storage and dispensing vessel.

A still further aspect of the invention relates in various embodiments to: a dispenser adapted to dispense material, operatively coupled with a monitoring system of the aforementioned type; a material utilizing apparatus adapted to receive material from a dispenser operatively coupled with a monitoring system of the aforementioned type; and an article manufactured using dispensed material monitored during dispensing by a monitoring system of the aforementioned type.

In another aspect, the invention relates to a system for monitoring fluid inventory in a fluid storage and dispensing vessel containing a storage medium having sorptive affinity for the fluid, from which the fluid is dispensed under dispensing conditions for use in a fluid-utilizing process, in which the system includes:

(a) a database of adsorption isotherm data for the fluid on the storage medium;
(b) a monitor adapted to monitor at least one fluid inventory-sensitive variable selected from among characteristics of the fluid storage and dispensing vessel, dispensing conditions, characteristics of the dispensed fluid, and characteristics of the fluid-utilizing process, and to responsively generate a monitoring signal correlative to the at least one fluid inventory-sensitive variable; and
(c) a processor adapted to receive the monitoring signal and to responsively conduct a signal processing operation correlating the at least one fluid inventory-sensitive variable with information in the database of adsorption isotherm data to generate an output indicative of fluid inventory in the fluid storage and dispensing vessel.

Another aspect of the invention relates to a system for monitoring fluid inventory in a fluid storage and dispensing vessel containing a fluid that is dispensed under dispensing conditions for use in a fluid-utilizing process, in which the system includes:

(a) a monitor adapted to monitor at least one fluid characteristic during dispensing of the fluid, and to responsively generate a monitoring signal correlative to the at least one fluid characteristic;
(b) a database of information relevant to determining inventory of fluid in the fluid storage and dispensing vessel during the dispensing; and
(c) a processor adapted to process the monitoring signal in a signal processing operation correlating the monitoring signal with information in the database to generate an output indicative of fluid inventory in the fluid storage and dispensing vessel.

In a further aspect, the invention relates to a system for monitoring fluid inventory in a fluid storage and dispensing vessel containing a fluid that is dispensed under dispensing conditions for use in a fluid-utilizing process, in which the system includes:

(a) a strain monitor adapted to monitor strain of the fluid storage and dispensing vessel during dispensing of the fluid, and to responsively generate a monitoring signal correlative to the strain;
(b) a database of information relevant to determining inventory of fluid in the fluid storage and dispensing vessel during the dispensing; and
(c) a processor adapted to process the monitoring signal in a signal processing operation correlating the monitoring signal with information in the database to generate an output indicative of fluid inventory in the fluid storage and dispensing vessel.

Still another aspect of the invention relates to a method of monitoring fluid in a fluid supply vessel during operation including dispensing of fluid from the fluid supply vessel, in which the method includes (i) monitoring a characteristic of the fluid supply vessel or the fluid dispensed therefrom, (ii) acquiring data from the monitoring, and generating data acquisition signal(s) correlative to the characteristic, and (iii) processing the data acquisition signal(s) and responsively generating an output indicative of inventory of fluid in the fluid supply vessel.

Yet another aspect of the invention relates to a method of monitoring material usage during operation including dispensing of material, said monitoring method including (i) monitoring a characteristic of the dispensing, (ii) acquiring data from such monitoring, and generating data acquisition signal(s) correlative to the characteristic, and (iii) processing the data acquisition signal(s) and responsively generating an output indicative of inventory of material available for dispensing.

A further aspect of the invention relates to a method of manufacturing semiconductor products in a semiconductor manufacturing facility, including an ion implanter including a gas box holding a dopant source fluid supply, in which such method includes monitoring at least one of temperature, pressure and flow rate of dopant source fluid dispensed from the dopant source fluid supply under dispensing conditions; acquiring data in the gas box from such monitoring; transmitting the acquired data to an output unit adapted to generate an output correlative to inventory of dopant source fluid in the dopant source fluid supply; and generating the output.

A still further aspect of the invention relates to a method of determining consumption of dopant source fluid in an ion implanter supplied with dopant source fluid from a dopant source fluid supply in a gas box of the ion implanter, wherein the dopant source fluid supply includes a sorbent medium having sorptive affinity for the dopant source fluid, and from which adsorbed dopant source fluid is desorbed under dispensing conditions, and the dopant source fluid supply includes a dopant source fluid storage and dispensing vessel of a predetermined size containing a predetermined weight of said sorbent medium, in which the method includes:

sensing gas box temperature T;
measuring the fluid storage and dispensing vessel pressure P;
setting an end-point pressure for dispensing dopant source fluid from the dopant source fluid storage and dispensing vessel;

determining temperature coefficients dP/dT at various pressures;

determining temperature coefficient for the end-point pressure;

normalizing measured pressure from the pressure monitor to a predetermined temperature;

normalizing the end-point pressure to the predetermined temperature;

determining isotherm equations at the predetermined temperature for the sorbent medium and dopant source fluid; and determining, using the isotherm equations, the amount of dopant source fluid remaining in the fluid storage and dispensing vessel.

In yet another aspect, the invention relates to a method of manufacturing a product comprising carrying out a manufacturing process utilizing a dispensed material, in which the method includes monitoring material usage of the dispensed material by a monitoring method as described above.

A further aspect of the invention relates to a method of monitoring fluid inventory in a fluid storage and dispensing vessel containing a storage medium having sorptive affinity for the fluid, from which the fluid is dispensed under dispensing conditions for use in a fluid-utilizing process, in which the method includes:

(a) providing a database of adsorption isotherm data for the fluid on the storage medium;

(b) monitoring at least one fluid inventory-sensitive variable selected from the group consisting of characteristics of the fluid storage and dispensing vessel, dispensing conditions, characteristics of the dispensed fluid, and characteristics of the fluid-utilizing process;

(c) generating a monitoring signal correlative to the at least one fluid inventory-sensitive variable;

(d) processing the monitoring signal in a signal processing operation correlating the at least one fluid inventory-sensitive variable with information in the database of adsorption isotherm data to generate an output indicative of fluid inventory in the fluid storage and dispensing vessel.

In another aspect, the invention relates to a method of monitoring fluid inventory in a fluid storage and dispensing vessel containing a fluid that is dispensed under dispensing conditions for use in a fluid-utilizing process, in which the method includes:

(a) monitoring at least one fluid characteristic during dispensing of the fluid;

(b) generating a monitoring signal correlative to the at least one fluid characteristic;

(c) providing a database of information relevant to determining inventory of fluid in the fluid storage and dispensing vessel during the dispensing; and (d) processing the monitoring signal in a signal processing operation correlating the monitoring signal with information in the database to generate an output indicative of fluid inventory in the fluid storage and dispensing vessel.

In another aspect, the invention relates to a method of monitoring fluid inventory in a fluid storage and dispensing vessel containing a fluid that is dispensed under dispensing conditions for use in a fluid-utilizing process, in which the method includes:

(a) monitoring strain of the fluid storage and dispensing vessel during dispensing of the fluid;

(b) generating a monitoring signal correlative to the strain;

(c) providing a database of information relevant to determining inventory of fluid in the fluid storage and dispensing vessel during the dispensing; and (d) processing the monitoring signal in a signal processing operation correlating the monitoring signal with information in the database to generate an output indicative of fluid inventory in the fluid storage and dispensing vessel.

A further aspect of the invention relates to a method of supplying material to a user at a use location from a remote supply location of the material, involving material dispensing by the user at the use location, in which the method includes (i) monitoring a characteristic of the dispensing, (ii) acquiring data from the monitoring, and generating data acquisition signal(s) correlative to the characteristic, (iii) processing the data acquisition signal(s) and responsively generating an output indicative of inventory of material available for dispensing, wherein processing is conducted at a billing location remote from a location of usage of the material and the output includes a bill for material dispensed at the location of usage of the material, and (iv) dispatching material from the remote supply location to the use location in response to the output indicative of inventory of material available for dispensing at the use location.

Other aspects, features and advantages of the invention will be more fully apparent from the ensuing disclosure and appended claims.

DETAILED DESCRIPTION

Figure 1:
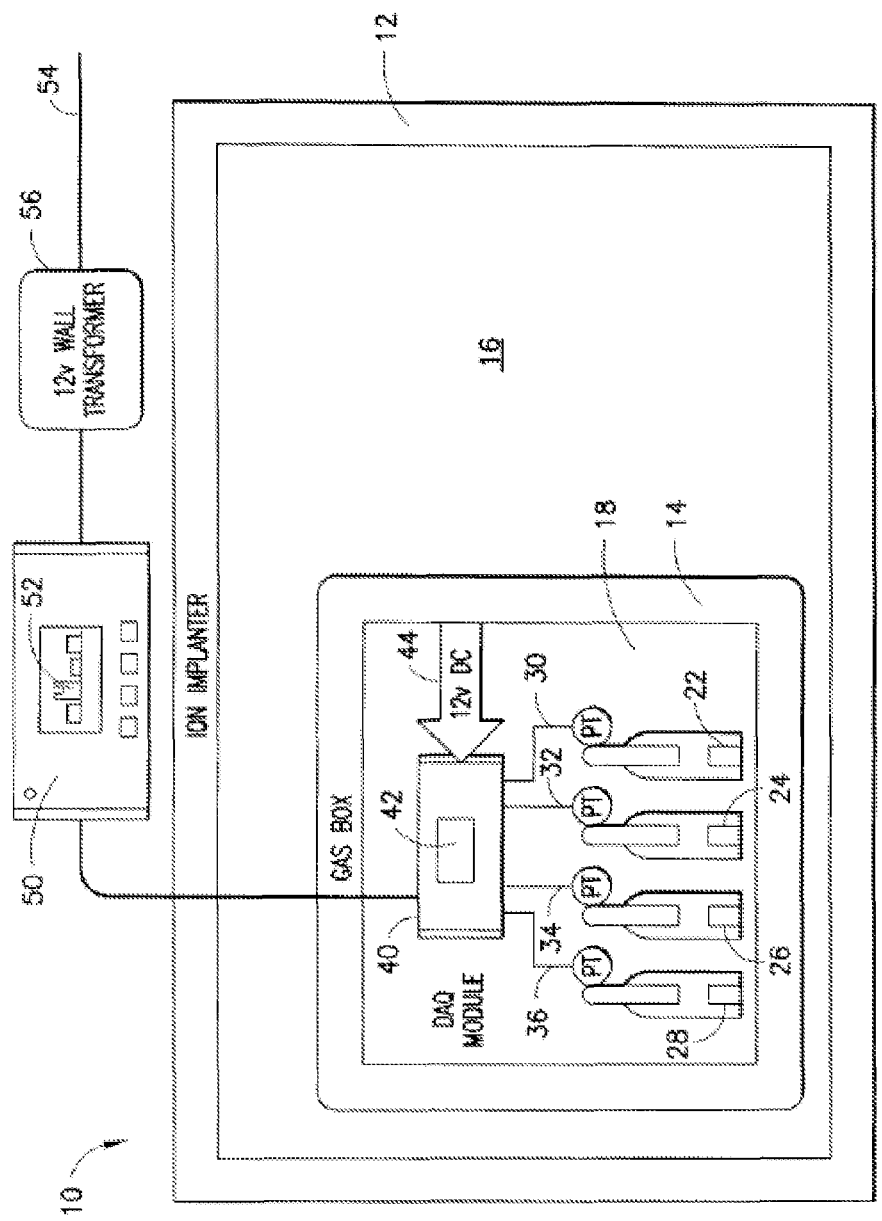
FIG. 1 is a schematic representation of an ion implanter utilizing an arrangement of fluid storage and dispensing vessels in the gas box of the implanter, in which fluid utilization is dynamically monitored by a fluid monitoring system, according to one embodiment of the invention.

The present invention provides a dynamic monitoring system and method that is usefully employed to monitoring fluid utilization in a fluid supply system, such as the fluid storage and dispensing systems of the types described in the Background of the Invention section hereof.

Although the dynamic monitoring system and method of the invention are described primarily hereinafter in reference to fluid for utilization in a semiconductor manufacturing operation, such as a dopant source gas for use in an ion implantation operation in the manufacture of semiconductor devices and device precursor structures, it will be recognized that the utility of the invention is not thus limited, but rather extends to and encompasses monitoring of materials of diverse character useful in diverse applications.

The monitoring system includes in a specific embodiment (i) one or more sensors for monitoring a characteristic of the fluid supply vessel or the gas dispensed therefrom, (ii) a data acquisition module operatively coupled to the one or more sensors, and (iii) a processing and display unit operatively coupled to the data acquisition module for determining utilization of the fluid in the fluid supply vessel and responsively outputting a graphical representation of fluid in the fluid supply vessel.

The one or more sensors for monitoring a characteristic of the fluid supply vessel in the dynamic fluid monitoring system of the invention may be of any suitable type, such as fluid sensors for sensing a selected characteristic of the fluid that is useful in determining the inventory and utilization rate of the gas. The selected characteristic of the fluid may for example include pressure of the fluid within the vessel or as it leaves the vessel, concentration of a specific component of the fluid within the vessel or in connecting lines between the vessel and downstream processing unit, temperature of the fluid within the vessel or in connecting lines between the vessel and downstream processing unit, flow rate of the fluid as the fluid leave the vessel or in connecting lines to the downstream processing unit, different mixture of gases both in the vessel and in connecting lines leaving the vessel, flow rate of purging gases in the connecting lines between the vessel and downstream processing system, etc., and the corresponding sensors may variously include pressure transducers, manometric pressure sensors, thermocouples, mass flow controllers, flow totalizers, etc.

Alternatively, the one or more monitoring sensors in the dynamic monitoring system of the invention may include one or more sensors for determining a characteristic of the fluid supply vessel itself, such as for example strain on the vessel wall of the fluid supply vessel where the fluid is contained at high pressure in the vessel, e.g., a vessel such as that of the VAC® fluid supply system (ATMI, Inc., Danbury, Conn., USA) described earlier herein, wherein the fluid is confined against a pressure regulator set to a predetermined set point pressure for dispensing of fluid from the vessel. Alternatively, the characteristic of the fluid supply vessel that may be employed for monitoring in accordance with the invention can be temperature of the fluid supply vessel, displacement or flexial character of the vessel, weight of the fluid supply vessel containing the fluid being or to be dispensed, etc. Still further, other devices that may be monitored include any pressure-reducing device that has a net effect in decreasing the interior pressure of a cylinder thereby reducing downstream pressure, such as restrictive flow orifice. Thus, by monitoring this type of device the operator would be assured that delivery pressures remained fixed and gas flow rates more closely matched the actual process needs downstream.

The processing and display unit that is coupled to the data acquisition module may utilize any suitable processing means, e.g., a general purpose programmable digital computer or central processing unit (CPU) including memory and processor components. The processor may be arranged to communicate with the memory by means of an address/data bus, and can be constituted by a commercially available or custom microprocessor. The memory can include, without limitation, devices of varied type, such as cache, ROM, PROM, EPROM, EEPROM, flash memory, SRAM, and DRAM.

The memory may include several categories of software and data used in the data processing system: the operating system; the application programs; the input/output (I/O) device drivers and the data. The data may include a database of known profiles of fluid storage and dispensing vessel characteristics, characteristics of various fluids, historical operating data for the gas-utilizing equipment being supplied with gas from the fluid storage and dispensing system, etc.

It will be appreciated that the operating system in the processing and display unit can be of any suitable type for use with a data processing system. Illustrative examples of operating systems that can be usefully employed include, without limitation, OS/2, AIX, OS/390 or System390 (International Business Machines Corporation, Armonk, N.Y.), Windows CE, Windows NT, Windows95, Windows98, Windows2000, or WindowsXP (Microsoft Corporation, Redmond, Wash.), Unix or Linux or FreeBSD, Palm OS from Palm, Inc., Mac OS (Apple Computer, Inc.), LabView or proprietary operating systems.

The I/O device drivers typically include software routines accessed through the operating system by the application programs to communicate with devices such as I/O data port(s), data storage and certain components of the memory.

The application programs are illustrative of the programs that implement the various features of the system and can suitably include one or more applications that support analysis of the data. The data represent the static and dynamic data used by the application programs, the operating system, the I/O device drivers, and other software programs that may reside in the memory.

Any configuration of the processor capable of carrying out the operations for the methodology of the invention can be advantageously employed.

The I/O data port of the processing and display unit can be used to transfer information between the processing and display unit and another computer system or a network (e.g., the Internet) or to other devices controllable by the processor.

The processing and display unit includes a display for graphically outputting the fluid utilization of the vessel(s) being monitored, e.g., in the form of a representation of the vessel(s) being monitored and its fluid content. This representation may be a "gas gauge" type of graphic depiction, in which the fluid content is shown in scale to the vessel schematically depicted in the graphical output, as a two-dimensional column having an upper bounding line representing the volumetric content of the fluid in the vessel, in which the upper bounding line is vertically downwardly translated in the display as the fluid is dispensed from the vessel and consumed in the external fluid-consuming facility that is being supplied with fluid from the vessel. Such type of depiction of the "fill status" of the vessel provides an intuitive and readily visually perceptible indication of the inventory of the fluid remaining in the vessel.

In a specific embodiment, the dynamic monitoring system of the invention may be employed to monitor an SDS® gas supply system, by monitoring pressure signals from pressure transducers operatively arranged to detect the pressure characteristic of gas being dispensed from the SDS® vessel. In another specific embodiment, the dynamic monitoring system may be employed to monitor a VAC® gas supply system, by monitoring a strain gauge on the VAC® vessel inside an ion implanter. The sensor-derived signals then are sent to the data acquisition module, from which send signals can be sent via a signal transmission line, e.g., a fiber optic communications link, to the processing and display unit, for display and archiving of the data in a nonvolatile buffer.

In another embodiment, the processing and display unit may also incorporate or be linked to alarming means, such as for example low pressure alarms indicating that the fluid storage and dispensing vessel is approaching a depletion end point.

The data acquisition module and the processing and display unit may be constructed and arranged to monitor multiple fluid supply and dispensing vessels, such as an array of such vessels in the gas box of an ion implanter in a fab.

The processing and display unit is suitably configured in one embodiment of the invention to calculate remaining usable volume of fluid in a fluid supply vessel based on known isotherm equations, vessel size and fluid type. This is highly advantageous because the volume of fluid remaining in a fluid supply vessel as it approaches exhaustion is not linear with pressure. As an illustrative example, with 100 torr of fluid pressure remaining in a 2.2 L AsH$_3$ SDS® cylinder, 50% of the deliverable arsine still remains in the vessel.

The monitoring system of the invention may be configured in a wide variety of ways, depending on the specific material processing operations and installations involved.

The monitoring system may for example be arranged for monitoring fluid in or from a fluid supply vessel during operation including dispensing of fluid from the fluid supply vessel, as including (i) one or more sensors for monitoring a characteristic of the fluid supply vessel or the fluid dispensed therefrom, (ii) a data acquisition apparatus operatively coupled to the one or more sensors to receive monitoring data therefrom and responsively generate an output correlative to the characteristic monitored by the one or more sensors, and (iii) a processor operatively coupled with the data acquisition apparatus and arranged to process the output from the data acquisition apparatus and responsively generate an output indicative of inventory of fluid in the fluid supply vessel.

The sensors in such monitoring system may include a pressure transducer adapted to monitor pressure of the fluid dispensed from the fluid supply vessel, and/or a mass flow sensor adapted to monitor flow rate of the fluid dispensed from the fluid supply vessel, and/or other suitable sensing devices and assemblies.

The monitoring system may be adapted for use in a fluid-utilizing facility containing the fluid supply vessel(s), one or more sensors, a data acquisition apparatus and a processor. The processor in one embodiment is located remotely from the fluid supply vessel(s), sensor(s) and data acquisition apparatus, e.g., in a fluid utilization billing facility remote from the fluid-utilizing facility.

In a specific embodiment incorporating such arrangement, a first data acquisition module may be provided in the fluid-utilizing facility and a second data acquisition module may be deployed in the fluid utilization billing facility. In this arrangement, the second data acquisition module is operatively coupled to the processor and to the first data acquisition module, e.g., by a communication modality including digital communication networks, signal transmission lines, and/or wireless communication modalities. The processor may be adapted to generate bills to the fluid-utilizing facility for the dispensed fluid, as well as reports of dispensed fluid.

In one preferred embodiment, the aforementioned communication modality includes an internet communication modality.

The fluid-utilizing facility in one implementation of the aforementioned monitoring system includes a semiconductor manufacturing facility including an ion implanter arranged in fluid supply relationship to the fluid supply vessel, with the fluid including a dopant source material for ion implantation. The output of the processor in such system may include a prompt or alert for change-out of the fluid supply vessel in the fluid-utilizing facility, and the system may be arranged and adapted for data logging of the monitored characteristic.

In a specific embodiment, the monitoring sensor(s) can include pressure transducer(s) producing analog electrical output(s) that are converted to light signal(s).

The invention contemplates in one embodiment a monitoring system for monitoring material usage during operation including dispensing of material, in which the monitoring system includes (i) one or more sensors for monitoring a characteristic of the dispensing, (ii) a data acquisition apparatus operatively coupled to the one or more sensors to receive monitoring data therefrom and responsively generate an output correlative to the characteristic monitored by the one or more sensors, and (iii) a processor operatively coupled with the data acquisition apparatus and arranged to process the output from the data acquisition apparatus and responsively generate an output indicative of inventory of material available for dispensing.

The processor in such embodiment can be situated at a billing location remote from the material usage location and the output can include a bill for material dispensed at the material usage location.

The aforementioned data acquisition apparatus can include a data acquisition module at the material usage location that is coupled in communication relationship with the remote billing location, including a communication modality selected from among digital information networks, wire communication, fiber optic communication, telemetry links and cellular communication. For example, the communication modality can include an internet, e.g., including servers supporting information protocols (e.g., XML) affording communication via the World Wide Web.

In another implementation, the processor in the monitoring system can include a portable digital device remote from the material usage location. The monitoring system can be adapted in various ways to convert monitoring data from one of more sensors to a digital form that is trackable using a wide variety of sensing, communication and processing/output devices.

The monitoring system in one preferred embodiment is adapted to monitor fluid usage of an ion implanter, with the processor being at a billing location remote from the ion implanter and the output of the processor including billing for the fluid usage.

The output of the data acquisition apparatus in monitoring systems of the invention may include material inventory data of the material that is available for dispensing, and the processor can be adapted to utilize algorithms to convert the material inventory data into usage information, and algorithms to convert to the usage data into customer invoice and usage reports for such material.

Thus, the invention in one specific aspect relates to a semiconductor manufacturing facility, including: an ion implanter including a gas box holding a dopant source fluid supply; at least one sensor adapted to monitor at least one of temperature, pressure and flow rate of dopant source fluid dispensed from the dopant source fluid supply under dispensing conditions; a data acquisition module installed in the gas box and adapted to receive monitoring signals from the sensor; an output unit adapted to generate an output correlative to inventory of dopant source fluid in the dopant source fluid supply; and a communication connection, e.g. a fiber optic communication line, between the data acquisition module and the output unit.

The dopant source fluid supply can include multiple fluid supply vessels, each having a dedicated pressure sensor associated therewith. As another variation, the data acquisition module may be configured to accommodate data logging via a data communications interface of the module and the data acquisition module can be configured to provide external alerting capability through relay contacts.

In a particular embodiment, a system is provided for determining consumption of dopant source fluid in an ion implanter supplied with dopant source fluid from a dopant source fluid supply in a gas box of the ion implanter, in which the dopant source fluid supply includes a sorbent medium having sorptive affinity for the dopant source fluid, and from which adsorbed dopant source fluid is desorbed under dispensing conditions. The dopant source fluid supply includes a dopant source fluid storage and dispensing vessel of a predetermined size containing a predetermined weight of said sorbent medium. The system includes:

a temperature sensor adapted to sense gas box temperature T;

a pressure monitor adapted for measuring the fluid storage and dispensing vessel pressure P; and a monitoring and control system operatively coupled to the temperature sensor and the pressure monitor, and adapted to conduct the steps of:

setting an end-point pressure for dispensing dopant source fluid from the dopant source fluid storage and dispensing vessel;

determining temperature coefficients dP/dT at various pressures;

determining temperature coefficient for the end-point pressure;

normalizing measured pressure from the pressure monitor to a predetermined temperature;

normalizing the end-point pressure to the predetermined temperature;

determining isotherm equations at the predetermined temperature for the sorbent medium and dopant source fluid; and determining, using the isotherm equations, the amount of dopant source fluid remaining in the fluid storage and dispensing vessel.

The monitoring system of the invention can be employed in combination with a material supply system adapted to supply material for the dispensing operation, with such material supply system including filled vessels of the material at a supply location and transport vehicles for delivery of filled vessels of the material from the supply location to a use location for the dispensing operation.

The invention correspondingly contemplates a dispenser adapted to dispense material, operatively coupled with the monitoring system of the invention. The invention further contemplates a material-utilizing apparatus adapted to receive material from a dispenser operatively coupled with the monitoring system of the invention, as well as articles manufactured using dispensed material monitored during dispensing by the monitoring system of the invention.

As one illustrative example, a system of the invention can be arranged for monitoring fluid inventory in a fluid storage and dispensing vessel containing a storage medium having sorptive affinity for the fluid, from which the fluid is dispensed under dispensing conditions for use in a fluid-utilizing process, in which the system includes:

(a) a database of adsorption isotherm data for the fluid on the storage medium;

(b) a monitor adapted to monitor at least one fluid inventory-sensitive variable selected from among characteristics of the fluid storage and dispensing vessel, dispensing conditions, characteristics of the dispensed fluid, and characteristics of the fluid-utilizing process, and to responsively generate a monitoring signal correlative to such at least one fluid inventory-sensitive variable; and (c) a processor adapted to receive the monitoring signal and to responsively conduct a signal processing operation correlating such at least one fluid inventory-sensitive variable with information in the database of adsorption isotherm data to generate an output indicative of fluid inventory in the fluid storage and dispensing vessel.

For example, the fluid inventory-sensitive variable(s) may be dispensed fluid pressure and/or dispensed fluid flow rate.

As another illustrative example, a system for monitoring fluid inventory in a fluid storage and dispensing vessel containing a fluid that is dispensed under dispensing conditions for use in a fluid-utilizing process can be constructed and arranged in accordance with the invention, to include:

(a) a monitor adapted to monitor at least one fluid characteristic during dispensing of the fluid, e.g., dispensed food pressure and/or dispensed fluid flow rate, and to responsively generate a monitoring signal correlative to such at least one fluid characteriandstic;

(b) a database of information relevant to determining inventory of fluid in the fluid storage and dispensing vessel during the dispensing; and (c) a processor adapted to process the monitoring signal in a signal processing operation correlating the monitoring signal with information in the database to generate an output indicative of fluid inventory in the fluid storage and dispensing vessel.

A further embodiment of the invention involves a system for monitoring fluid inventory in a fluid storage and dispensing vessel containing a fluid that is dispensed under dispensing conditions for use in a fluid-utilizing process, in which the system includes:

(a) a strain monitor, e.g., one or more strain gauges mounted on an exterior surface portion of the fluid storage and dispensing vessel, adapted to monitor strain of the fluid storage and dispensing vessel during dispensing of the fluid, and to responsively generate a monitoring signal correlative to the strain;

(b) a database of information relevant to determining inventory of fluid in the fluid storage and dispensing vessel during the dispensing; and (c) a processor adapted to process the monitoring signal in a signal processing operation correlating the monitoring signal with information in the database to generate an output indicative of fluid inventory in the fluid storage and dispensing vessel.

The information in the database of such system can be of any suitable type, including for example information such as compressibilities of the fluid under varied dispensing conditions, fluid storage and dispensing vessel characteristics, fluid molecular weight information, and PVT relationships applicable to the fluid, etc.

The invention therefore provides a method of monitoring fluid in a fluid supply vessel during operation including dispensing of fluid from the fluid supply vessel. In an illustrative technique, such method can include the steps of: (i) monitoring a characteristic of the fluid supply vessel or the fluid dispensed therefrom, (ii) acquiring data from such monitoring, and generating data acquisition signal(s) correlative to the characteristic, and (iii) processing the data acquisition signal(s) and responsively generating an output indicative of inventory of fluid in the fluid supply vessel. The monitoring in such method can be pressure monitoring of fluid dispensed from the fluid supply vessel and/or monitoring of the flow rate of the dispensed fluid.

The fluid after dispensing can be used in a fluid-utilizing facility, and the processing can be conducted remotely in relation to the location of the use of fluid dispensed in the dispensing operation, e.g., in a fluid utilization billing facility remote from the fluid-utilizing facility.

Another method aspect of the invention relates to monitoring material usage during operation including dispensing of material, including the steps of: (i) monitoring a characteristic of the dispensing, (ii) acquiring data from such monitoring, and generating data acquisition signal(s) correlative to the characteristic, and (iii) processing the data acquisition signal(s), e.g., at a billing location remote from a location usage of the material, and responsively generating an output indicative of inventory of material available for dispensing, e.g., an output including a bill for material dispensed at said location of usage of said material. The data acquisition step may include use of a data acquisition module at the location of use that is coupled with the billing location as previously described, e.g., by an internet connection in which the internet includes servers supporting information protocols affording communication via the World Wide Web. The methodology may be conducted as a Web service, or in other manner using fixed and/or mobile processing resources.

In one embodiment, the invention contemplates a method of manufacturing semiconductor products in a semiconductor manufacturing facility, including an ion implanter including a gas box holding a dopant source fluid supply, in which the method includes monitoring at least one of temperature, pressure and flow rate of dopant source fluid dispensed from the dopant source fluid supply under dispensing conditions; acquiring data in the gas box from such monitoring; transmitting the acquired data to an output unit adapted to generate an output correlative to inventory of dopant source fluid in the dopant source fluid supply; and generating such output.

In another embodiment, the invention contemplates a method of determining consumption of dopant source fluid in an ion implanter supplied with dopant source fluid from a dopant source fluid supply in a gas box of the ion implanter, wherein the dopant source fluid supply includes a sorbent medium having sorptive affinity for the dopant source fluid, and from which adsorbed dopant source fluid is desorbed under dispensing conditions, and the dopant source fluid supply includes a dopant source fluid storage and dispensing vessel of a predetermined size containing a predetermined weight of said sorbent medium. The method includes the steps of:

sensing gas box temperature T;
measuring the fluid storage and dispensing vessel pressure P;
setting an end-point pressure for dispensing dopant source fluid from the dopant source fluid storage and dispensing vessel;
determining temperature coefficients dP/dT at various pressures;
determining temperature coefficient for the end-point pressure;
normalizing measured pressure from the pressure monitor to a predetermined temperature;
normalizing the end-point pressure to the predetermined temperature;
determining isotherm equations at the predetermined temperature for the sorbent medium and dopant source fluid; and
determining, using the isotherm equations, the amount of dopant source fluid remaining in the fluid storage and dispensing vessel.

The method of the invention may be conducted in combination with a material supply operation including supplying material for the dispensing operation, and the material supply operation can include provision of filled vessels of the material at a supply location and transport of filled vessels of the material from the supply location to a use location for such dispensing.

A product can correspondingly be manufactured by carrying out a manufacturing process utilizing a dispensed material appropriate to its manufacture, with monitoring of the material usage of the dispensed material by a monitoring method of the invention.

A further aspect of the invention involves a method of monitoring fluid inventory in a fluid storage and dispensing vessel containing a storage medium having sorptive affinity for the fluid, from which the fluid is dispensed under dispensing conditions for use in a fluid-utilizing process. The method includes the steps of:

(a) providing a database of adsorption isotherm data for the fluid on the storage medium;
(b) monitoring at least one fluid inventory-sensitive variable selected from the group consisting of characteristics of the fluid storage and dispensing vessel, dispensing conditions, characteristics of the dispensed fluid, and characteristics of the fluid-utilizing process;
(c) generating a monitoring signal correlative to the at least one fluid inventory-sensitive variable;
(d) processing the monitoring signal in a signal processing operation correlating the at least one fluid inventory-sensitive variable with information in the database of adsorption isotherm data to generate an output indicative of fluid inventory in the fluid storage and dispensing vessel.

Another method of the invention includes monitoring fluid inventory in a fluid storage and dispensing vessel containing a fluid that is dispensed under dispensing conditions for use in a fluid-utilizing process, in which the method includes:

(a) monitoring at least one fluid characteristic during dispensing of the fluid;
(b) generating a monitoring signal correlative to the at least one fluid characteristic;
(c) providing a database of information relevant to determining inventory of fluid in the fluid storage and dispensing vessel during said dispensing; and
(d) processing the monitoring signal in a signal processing operation correlating the monitoring signal with information in the database to generate an output indicative of fluid inventory in the fluid storage and dispensing vessel.

A further methodology of the invention includes monitoring fluid inventory in a fluid storage and dispensing vessel containing a fluid that is dispensed under dispensing conditions for use in a fluid-utilizing process, in which the method includes the steps of:

(a) monitoring strain of the fluid storage and dispensing vessel during dispensing of the fluid;
(b) generating a monitoring signal correlative to the strain;
(c) providing a database of information relevant to determining inventory of fluid in the fluid storage and dispensing vessel during the dispensing; and
(d) processing the monitoring signal in a signal processing operation correlating the monitoring signal with information in the database to generate an output indicative of fluid inventory in the fluid storage and dispensing vessel.

The database information in such method can include information such as compressibilities of the fluid under varied dispensing conditions, fluid storage and dispensing vessel characteristics, fluid molecular weight information, and PVT relationships applicable to the fluid.

The invention in another implementation contemplates a method of supplying material to a user at a use location from a remote supply location of said material, involving material dispensing by the user at said use location, in which the method includes (i) monitoring a characteristic of the dispensing, (ii) acquiring data from the monitoring, and generating data acquisition signal(s) correlative to the characteristic, (iii) processing the data acquisition signal(s) and responsively generating an output indicative of inventory of material available for dispensing, wherein processing is conducted at a billing location remote from a location of usage of said material and the output includes a bill for material dispensed at the location of usage of the material, and (iv) dispatching material from the remote supply location to the use location in response to the output indicative of inventory of material available for dispensing at the use location.

Referring now to the drawings, FIG. 1 is a schematic representation of a fab installation 10 including an ion implanter 12 utilizing an arrangement of fluid storage and dispensing vessels 22, 24, 26 and 28 in the gas box 14 of the implanter, in which fluid utilization is dynamically monitored by a fluid monitoring system, according to one embodiment of the invention.

As schematically illustrated, the ion implanter 12 includes a containment structure defining an interior volume 16 containing the gas box 14. The gas box in turn defines an interior volume 18 in which is disposed an array of fluid storage and dispensing vessels 22, 24, 26 and 28, each of which has an associated pressure transducer ("PT"), e.g., disposed in a valve head of the vessel assembly and arranged to sense the fluid pressure of fluid dispensed from the associated vessel.

The pressure transducers associated with the vessels 22, 24, 26 and 28 generate signals correlative to the sensed pressure in each dispensing operation (the flow circuitry associated with the fluid supply and dispensing vessels, and the details of the ion implantation apparatus in the ion implanter containment structure not being shown, for ease of description) and such signals are transmitted by the signal transmission lines 30, 32, 34 and 36 to the data acquisition module 40.

The data acquisition module comprises a housing 42 containing associated electronics and acquisition hardware, in a unitary configuration. The data acquisition module 40 receives power from a suitable power supply (e.g., a 12 volt DC supply) schematically indicated by arrow 44 in FIG. 1.

The data acquisition module 40 serves to acquire the sensing signals from the sensors associated with the vessels and process the signals into a suitable form for transmission to the processor and display unit 50 by means of signal transmission line 48, such as a fiber optic cable, extending from the data acquisition module 40 through the wall of the gas box 14 and the enclosing wall of the ion implanter 12, to the processor and display unit 50. Notably, in the alternative, the acquisition module can receive the sensing signals via a wireless communications means such as a device that transmits via radio frequency.

The processor and display unit 50 includes signal processing means as previously described herein, which processes the signals transmitted by the signal transmission line 48 to produce a graphical output that is displayed on the display 52 of the unit 50. The processor and display unit 50 is powered by a suitable power supply, e.g., by a power cord 54 operatively coupled with a transformer 56, e.g., a 12 volt wall transformer, and adapted for plug-in to a wall socket of an electrical supply network, e.g., a 110-volt or 220-volt service.

Figure 2:
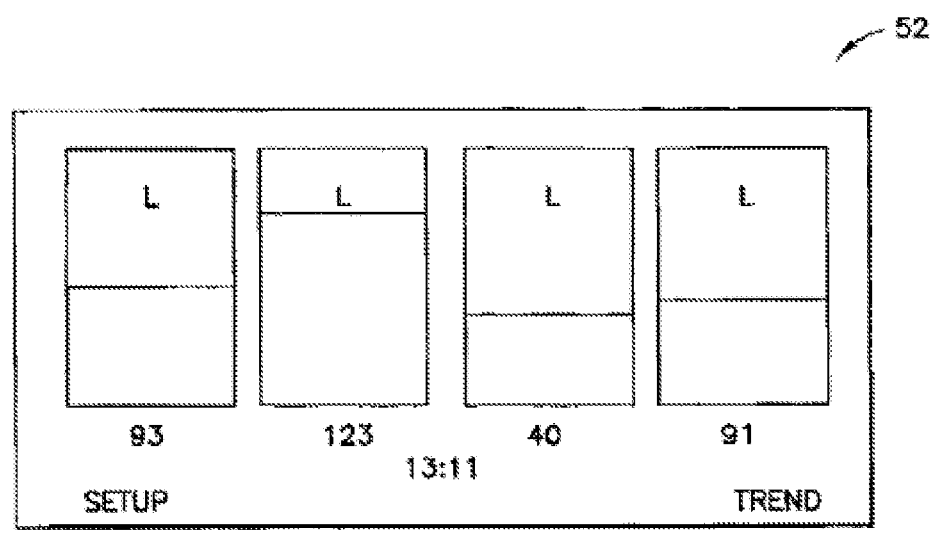
FIG. 2 is a schematic representation of the visual display interface of a visual display unit of the fluid monitoring system shown in FIG. 1.

FIG. 2 is a schematic representation of the visual display interface of the visual display unit 50 of the fluid monitoring system in the fab installation 10 shown in FIG. 1.

As illustrated, the visual display interface shows graphical depictions of each of the four vessels 22, 24, 26 and 28 in the gas box 14 of the installation 10, in the form of two-dimensional vertically extending rectangles having a horizontal line depicting the boundary of the fluid inventory in each rectangle.

In the specific example shown, the fluid inventory is shown by a white "fill volume" which in relation to the total area of the associated rectangle indicates the amount of the fluid remaining in the vessel at any given time. By such output, the status of each of the monitored vessels is readily apparent at a glance, as to its fluid inventory. The display may also, as in the illustrative display shown in FIG. 2, also provide a numerical indication of the relative fluid filled state of the respective vessels (e.g., as shown by the numerical indicia "93", "123", "40" and "91" in the display depicted in FIG. 2).

The monitoring process may be carried out in any suitable manner, as regards transmission of sensed data to the data acquisition module 40, for monitoring in a real-time, continuous fashion as desired in a given application of the invention.

Regarding specific embodiments of the dynamic monitoring system shown in FIG. 1 and FIG. 2, the processor and display unit may be equipped for interfacing with a computer, e.g., in an operator station in the fab. The processor and display unit may for example be equipped with an RS-232 port for such purpose, to enable cabling between such RS-232 port on the processor and display module, and a serial port on an operator computer. The data acquisition module may be suitably configured for providing sensor excitation and analog input for each of the sensors associated with the vessels. When the sensors are strain gauges mounted on the walls of the fluid storage and dispensing vessels, such sensors may be readily cabled to the data acquisition module.

The processor and display unit in a specific embodiment is arranged for data logging with archiving of up to 3000 data points, with logging rates configured from a setup menu to a suitable value in a range of from 5 seconds per point to 2 hours per point. All four channels for the four vessels in the illustrative installation are logged and logging data is downloadable through an RS-232 port of the processor and display unit. A trend graph may be provided for each of the four monitored channels, scaled to match the bar graph 100% (indicating complete fluid inventory in the vessel) and to show the entire data log buffer. Since the display is 100 points wide and the data log is 3000 points wide, the display shows an average of 300 readings per pixel on the display. For finer viewing, data may be downloaded from the processor and display unit via the RS232 port. The processor and display unit in a specific embodiment is configured so that each data element is time stamped by the processor.

By means of a dynamic monitoring system of the general type described in connection with FIGS. 1 and 2, fluid storage and dispensing vessels can be readily monitored by a simple arrangement of the pressure transducers associated with the specific vessels. The vessels that may be monitored by systems of the invention include SDS® fluid storage and dispensing vessels commercially available from ATMI, Inc. (Danbury, Conn., USA) and vessels variously described in U.S. Pat. Nos. 5,518,528; 5,704,965; 5,704,967; and 5,707,424, high-pressure vessels of the conventional types, VAC® fluid storage and dispensing vessels commercially available from ATMI, Inc. (Danbury, Conn., USA) and vessels variously described in U.S. Pat. Nos. 6,101,816; 6,089,027; 6,360,546; 6,474,076; and 6,343,476, and solid source reagent storage and fluid dispensing vessels of the type described in U.S. Provisional Patent Application No. 60/662,515 filed Mar. 16, 2005 in the names of Paul J. Marganski, James A. Dietz and Joseph D. Sweeney for "System for Delivery of Reagents from Solid Sources Thereof," the disclosures of the all of which are hereby incorporated by reference in their respective entireties, for all purposes.

In VAC® fluid storage and dispensing vessels, in lieu of a pressure transducers, there may be employed strain monitor devices associated with the vessel, such as a resistance strain gauge mounted on the outer wall of the vessel to monitor deflection of the vessel wall during fluid dispensing operation. Strain monitoring systems of such type are described, for example, in U.S. Pat. No. 6,494,343 issued Dec. 17, 2002, the disclosure which hereby is incorporated by reference, in its entirety, for all purposes.

More generally, however, any suitable monitoring device, assembly or unit may be employed, that is useful for monitoring a fluid inventory-related characteristic of the fluid vessel, dispensed fluid, flow circuitry, or other aspect of the fluid storage and dispensing system.

The system of the invention permits fluid inventory to be monitored in an intermittent or continuous manner, as may be desirable or necessary in a given application of the invention, and additionally permits the user to implement the system with outputted prompts or alerts (e.g., alarms, voice and/or e-mail reminders for vessel change-out) so that downtime in the fluid-utilizing facility is minimized.

The inventive system also provides a simple and effective user interface for data logging that may be implemented in any convenient manner, e.g., in a system utilizing relay contacts for actuation of the processor and display unit.

The fluid inventory monitoring and display system when configured as illustratively shown and described with reference to FIGS. 1 and 2 is readily installed in a semiconductor manufacturing facility, with the data acquisition module being powered by a 12 V DC power source and installed in a secure mounting location in the gas box of the semiconductor facility, with fiber optic communication being routed from the data acquisition module in the gas box, to an external display unit. Installation of systems of such type may for example require 2-8 hours, and are thus readily accommodated in retrofitting of existing semiconductor manufacturing systems.

When pressure transducers are employed for monitoring of dispensed fluid pressure in the practice in the present invention, any suitable pressure transducer devices can be employed that are appropriate to the specific implementation of the fluid inventory monitoring and display system. One preferred pressure transducer is a Staset® solid-state pressure transducer, commercially available from United Electric Controls, Precision Sensors Division (Milford, Conn., USA). The transducer advantageously is installed at or near the connection of the fluid storage and dispensing vessel with the associated flow circuitry, e.g., at or near the "pigtail" connection of the manifold to which the fluid storage and dispensing vessel may be coupled in flow communication relationship.

In one preferred implementation of the fluid inventory monitoring system of the invention, the system is adapted to monitor up to four ion implant or dopant vessels at positive or sub-atmospheric pressure, within accuracy of ±5 torr, by the onboard data acquisition display unit. In such implementation, analog voltage from each pressure transducer is converted to light pulses, which then are transmitted across the ion implanter high voltage gradient to a programmable display unit at ground potential. The monitoring system in such implementation is a stand-alone system, so that there is no interface necessary with the implanter operating system, and provides continuous monitoring of the implanter dopant supply vessels, even during wafer processing. The programmable display unit displays each dopant vessel pressure and fill level, and is programmable to provide the user with flexible choice of pressure units for display, as well as preemptive vessel empty alerts. The system accommodates data logging through an appropriate interface of the data acquisition module, e.g., an RS-232 interface or other suitable data communications interface, with external alerting capability through relay contacts.

In such illustrative implementation, the data acquisition module converts analog pressure signals into light pulses and transmits them through the fiber optic pipes for graphical display on the display unit of the system. The fiber-optic light pipes provide a transmission pathway for light pulses from the data acquisition module to the display unit. The display module displays implanter gas line graphical pressure and dopant vessel fill level.

In another aspect of the invention, the operational cost burden on semiconductor manufacturing facilities deriving from the aforementioned requirements of US GAAP for expensing of entire volumes of purchased specialty chemicals for use in semiconductor manufacturing operations is relieved by a fluid inventory monitoring and billing system that permits the fluid user to pay for high-value specialty materials as they are consumed.

The invention in such respect provides a system and method for monitoring the amount of a specialty material consumed by a purchaser over time and for accurately levying appropriate charges for such specialty material. Such aspect of the invention utilizes the fluid inventory monitoring system of the invention in an implementation including a transmitter for transmission of digital information from the fluid-utilizing installation to a billing installation remote therefrom.

The transmission of the fluid inventory monitoring information may be effected in any suitable manner, such as by use of a digital information network (e.g., an intranet, extranet, and/or internet), a dedicated wire or fiber-optic cable communications link, telemetry system, cellular communications network, etc.

In one embodiment, the fluid inventory monitoring information is transmitted to the billing installation by an internet communications network. For example, the network may include servers supporting information protocols, such as HTTP, affording communication via the World Wide Web.

In another illustrative implementation, the fluid inventory monitoring and billing system may be adapted and implemented as a Web service system, in which software functionality is provided over the Internet and extensible markup language (e.g., XML) messages are used to communicate from the data acquisition module in the fluid-utilizing facility to the billing installation of the fluid provider.

The billing installation of the fluid provider may include a remote data acquisition unit, e.g., a DAQ module, or other data reception interface for receipt of transmitted fluid utilization data from the fluid-utilizing facility, operatively coupled with a computer or other processor, e.g., a general-purpose programmable computer, microprocessor, programmable logic unit or other computational module adapted to store the fluid inventory data transmitted from the semiconductor manufacturing facility, as well as to store algorithms to convert the fluid inventory data into usage information, and algorithms to convert to the usage data into customer invoice and usage reports.

By such arrangement, customers can pay for high-value specialty material as it is consumed, rather than paying large sums of money up front, so that initial cash outlay is avoided. Additionally, such arrangement enables the supplier to monitor material usage by the user and to better manage inventory levels and shipments/deliveries of material, which inures to the benefit of the specialty material user. The supplier is also enabled by such arrangement to troubleshoot maintenance issues involving onboard systems from the monitoring and billing center.

In another implementation, the inventory monitoring data may be transmitted to a mobile location, remote from the use facility, such as when the overall system is configured and adapted so that the inventory data are accessible remotely by personal digital assistant (PDA), portable computer, Internet-enabled telephone, or other mobile device, so that any troubleshooting, scheduling of use facility visits, etc. can be accommodated by a service technician, material supplier representative, or other person or portable installation.

By way of illustrative example, a semiconductor manufacturing facility including an ion implanter can be modified with deployment of a monitoring and billing system of the present invention. The implanter may utilize as a dopant source an SDS® vessel (ATMI, Inc., Danbury, Conn., USA) containing a dopant precursor fluid such as arsine or phosphine at sub-atmospheric pressure. The implanter is arranged with a monitoring system of the invention, providing pressure and flow monitoring capability, including a signal board that receives pressure and/or flow rate measurements, with outputs in volts or amps. The signal board converts the electrical signal so that it can be transmitted by fiber optic cable across the voltage gap of the implanter. The light signal then is converted to a digital electrical signal and transmitted from a local data acquisition module to a remote fluid supplier data acquisition module. From the remote fluid supplier data acquisition module, the utilization information is stored, analyzed and used to generate usage reports, customer invoices, replenishment requests, and/or warnings of impending exhaustion of the fluid supply vessel, by means of a supplier installation computer/printer assembly, coupled with the supplier data acquisition module.

Figure 3:
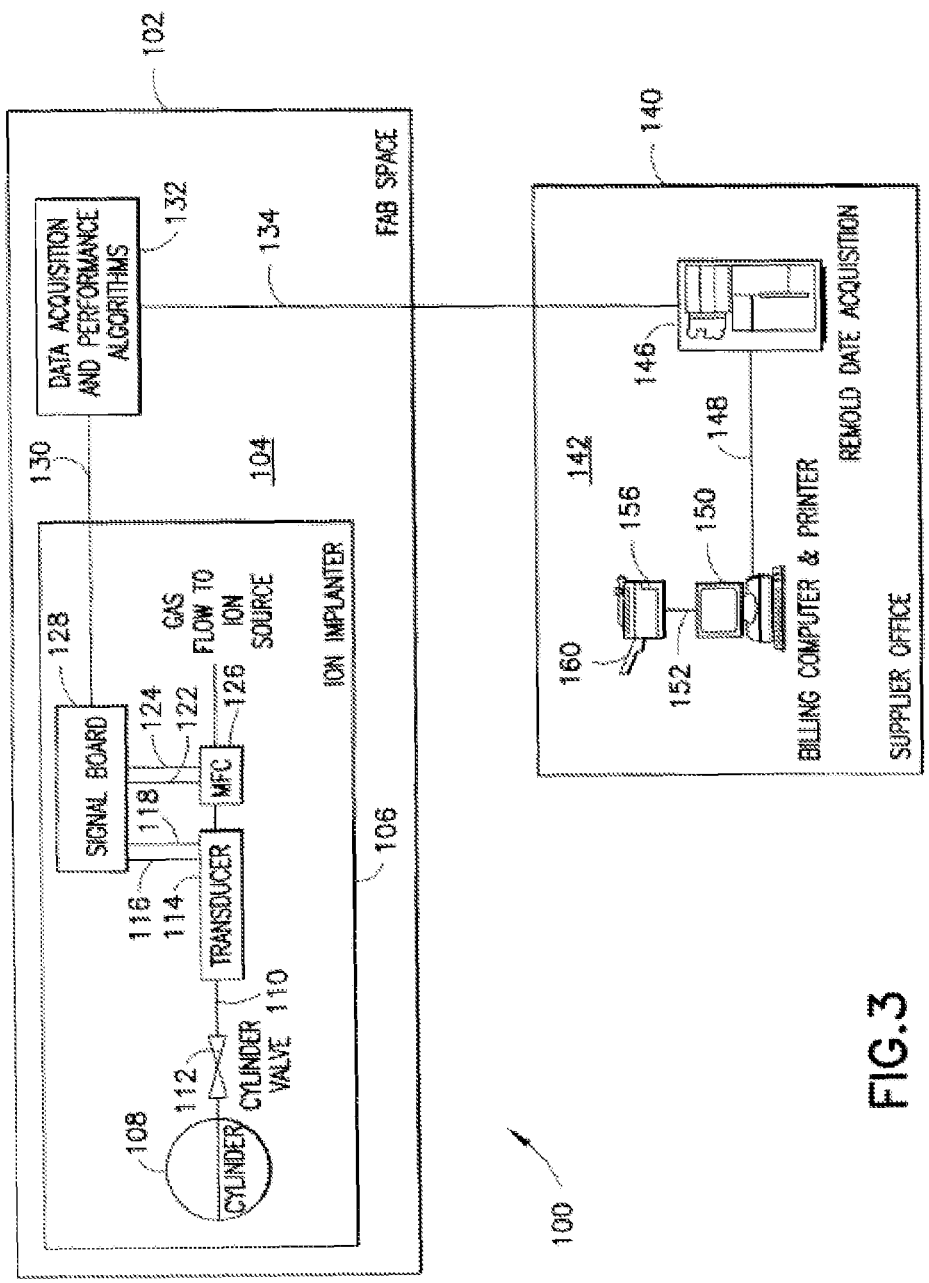
FIG. 3 is a schematic representation of a semiconductor manufacturing facility arranged in data communication relationship with a supplier office that is monitoring fluid utilization from a fluid source in the semiconductor manufacturing facility, according to another embodiment of the invention.

FIG. 3 is a schematic representation of a semiconductor manufacturing facility arranged in data communication relationship with a supplier office that is monitoring fluid utilization from a fluid source in the semiconductor manufacturing facility, according to another embodiment of the invention.

The fluid source monitoring and billing system 100 includes a semiconductor manufacturing facility 102 including a structural space 104 in which is disposed an ion implanter 106. The ion implanter 106 includes a fluid storage and dispensing apparatus including a fluid storage and dispensing vessel 108 coupled with a fluid dispensing line 110.

The fluid dispensing line 110 is coupled at its outlet end with an ion source unit (not shown in FIG. 3). The ion source unit is adapted to generate ionized dopant species for impingement on a wafer or other substrate article to produce a corresponding doped article.

The fluid dispensing line 110 is joined in flow communication with a flow control valve 112 associated with the fluid storage and dispensing vessel. The flow control valve 112 may be part of a valve head structure joined to the fluid storage and dispensing vessel of the fluid storage and dispensing apparatus, or it may be separate and distinct from such apparatus, and may be constituted by a mechanical valve with a pneumatic actuator, by a solenoid valve operably coupled with a suitable power supply for actuation of the valve, or other device or assembly that is selectively operable to modulate flow of the fluid from the storage and dispensing vessel during the dispensing operation.

In the arrangement shown in FIG. 3, pressure of the dispensed fluid in the dispensing line 110 during fluid dispensing operation is monitored by a pressure transducer 114 disposed in such dispensing line. The pressure transducer 114 is in communication with a signal board 128 by signal transmission lines 116 and 118, whereby a sensed pressure signal is communicated in line 116 to the signal board 128, and control and/or power signals can be sent from the signal board to the transducer in line 118.

In like manner, a mass flow controller 126 is disposed in the dispensing line 110 and is coupled in signal communication relationship with the signal board 128 by the signal transmission lines 122 and 124. By such signal transmission lines, a sensed mass flow rate can be communicated in signal transmission line 122 to the signal board 128, and a control signal and/or power signal can be communicated by the signal board to the mass flow controller in signal transmission line 124.

The signal board 128 is coupled in signal transmission relationship with a data acquisition and performance algorithms unit 132 (referred to as a DAQ module), which is coupled in signal communication relationship with the signal board by the signal transmission line 130. The DAQ module 132 provides power to the transducer and mass flow controller, and reads the transducer and mass flow controller outputs, conducts an analog-to-digital (A/D) conversion, and produces a digital output corresponding to the pressure and/or flow rate of the dispensed fluid.

The signal transmission line 130 connecting the DAQ module 132 and the signal board in one embodiment includes a fiber optic cable arranged for signal transmission.

By the arrangement shown in FIG. 3, the analog outputs of fluid pressure from the pressure transducer 114 and/or fluid flow rate from the mass flow controller 126 are passed to the signal board. The signal board converts such analog input to output indicative of the pressure and/or flow rate of the fluid being dispensed, which is outputted in line 130 to the DAQ module 132.

The DAQ module 132 in turn is coupled in communication relationship with a supplier office 140 by a communication link 134 schematically indicated in FIG. 3. The communication link 134 can be of any suitable type, including for example a wired or wireless connection, such as connection via a global data communications network, e.g., Internet-1 or Internet-2, communication by a satellite communications network, DSL network, dedicated fiber optic line, cable modem connection, or by any other communications link that permits signals correlative with the usage of the fluid in the semiconductor manufacturing facility to be communicated to a facility or installation of the fluid supplier.

The supplier office 140 includes a structural space 142 containing data receiving, data processing and billing apparatus.

In the supplier office 140, the communications link 134 couples to a remote data acquisition module 146, as a supplier-side DAQ module that receives the output indicative of the pressure and/or flow rate of the fluid being dispensed in semiconductor manufacturing facility 102, as transmitted from the DAQ module 132 in such manufacturing facility. Based on the output from the manufacturing facility DAQ module 132 transmitted by communications link 134, a usage-correlated signal is transmitted by the supplier side DAQ module 146 in signal transmission line 148 to the billing computer 150.

Based on the usage-correlated signal received in line 148 from the supplier side DAQ module 146, the billing computer 150 computes a charge to the semiconductor facility based on the usage of the fluid from the fluid storage and dispensing vessel 108 furnished to the manufacturing facility 102. The computed charge then is communicated in the output communicated from the billing computer 150 by cable printer 152 to printer 156, for printing of a bill 160 to the semiconductor manufacturing facility 102.

By an arrangement of the type illustratively described in connection with FIG. 3, a fluid supplier can monitor the usage of the fluid in the fluid-utilizing facility, and correspondingly bill the facility on a current use basis, on a schedule and at a frequency that is appropriate to the specific fluid(s) being supplied. For example, the fluid-utilizing facility may be billed at predetermined time intervals, e.g., monthly or bi-monthly, or as a specific volumetric usage-based billing, e.g., for each liter of fluid cumulatively dispensed from a fluid supply vessel, or on other suitable basis.

The features, operation and advantages of the invention are more fully described with reference to the following non-limiting example of an illustrative embodiment of the invention.

EXAMPLE

This example illustrates the procedures used to estimate the usable gas in a gas storage and dispensing system of a type commercially available under the trademark SDS2 from ATMI, Inc. (Danbury, Conn.) and more fully described in U.S. Pat. Nos. 5,518,528; 5,704,965; 5,704,967; and 5,707,424. Such gas storage and dispensing system includes a gas storage and dispensing vessel containing a bead activated carbon adsorbent having sorptive affinity for the semiconductor manufacturing gas held in the interior volume of the vessel. The gas may be of any suitable type, e.g., arsine, phosphine, boron trifluoride, germanium tetrafluoride, and silicon tetrafluoride, and the gas may be retained in the vessel for dispensing therefrom at suitable pressure, e.g., a subatmospheric pressure in a range of 200 to 700 torr.

The illustrative gas storage and dispensing system is deployed in an ion implanter of the type schematically shown in FIG. 1 hereof, equipped with a dynamic fluid utilization monitoring system of the invention. The dynamic fluid monitoring system in this embodiment includes a processing and display unit, a data acquisition module, and fluid sensors for sensing a selected characteristic of the fluid that may be used to determine the inventory and utilization rate of the gas. The fluid sensors in this embodiment include pressure transducers, each of which is operatively coupled with one of the multiple gas storage and dispensing vessels as schematically shown in FIG. 1.

The processing and display unit is programmably arranged to estimate the amount of usable gas remaining in the SDS2 vessel at a given pressure and temperature. The dynamic monitoring system of the invention can be used to estimate the service life of a gas storage and dispensing vessel used in the implanter.

In the utilization determination, the following symbols and units are employed.

T Gasbox temperature, ° C.
P Pressure transducer reading, torr or mmHg
$P_{21}$ Normalized pressure reading, torr or mmHg
$P_{end-21}$ Normalized end point pressure, torr or mmHg
$C_{lo}$ Pressure change per degree ° C. when temperature is less than 21° C., torr/° C.
$C_{mid}$ Pressure change per degree ° C. when temperature is between 21-26° C., torr/° C.
$C_{hi}$ Pressure change per degree ° C. when temperature is less than 26-33° C., torr/° C.
$C_{end-lo}$ Pressure change per degree ° C. for end point pressure (less than 21° C.), torr/° C.
$C_{end-mid}$ Pressure change per degree ° C. for end point pressure (21-26° C.), torr/° C.
$C_{end-hi}$ Pressure change per degree ° C. for end point pressure (26-33° C.), torr/° C.
CW Carbon weight in the cylinder, gram
MW Molecular weight of the gas
sccm Gas flow rate to the ion source, ml/min
G The amount gas in grams remained in the cylinder, gram
V The amount gas in cubic centimeter remained in the cylinder, ml
HR Number of hours left before the cylinder is empty, hour.
4× 2.2 liter SDS® cylinder, also called JY size
7× 0.4 liter SDS® cylinder, also called WY size
3× 6.6 liter SDS® cylinder, also called UY size The utilization determination is carried out by the following steps:

Step 1:
Measure or determine the implanter gasbox temperature T (° C.)

Step 2:
Determine the gas storage and dispensing vessel size and weight of sorbent material therein. For example, the vessel size may be 4×, 7× or 3×. The sorbent then may have a carbon sorbent material disposed in the vessel, having a carbon weight (CW) in grams, which is dependent on the vessel size. If the vessel size is 4×, then the CW is 1275. If the vessel size is 7×, then the CW is 239. If the vessel size is 3×, then the CW is 3825.

Step 3:
Set the end-point pressure $P_{end}$ of the fluid storage and dispensing system, e.g., an end-point pressure $P_{end}$ of 5 torr.

Step 4:
Measure the vessel pressure reading, P.

Step 5:
Determine the temperature coefficients, dP/dT, at various pressures.

For example:
If T is less than 21° C.:

$$C_{lo}=0.04079168*(P^{0.9623277})$$

If T is between 21 to 26° C.:

$$C_{mid}=0.07282172*(P^{0.8938195})$$

If T is less than 26 to 33° C.:

$$C_{hi}=0.08678193*(P^{0.8914468})$$

Step 6:
Determine the temperature coefficient for the end point pressure.

For example:
If T is less than 21° C.:

$$C_{end-lo}=0.04079168*(P_{end}^{0.9623277})$$

If T is between 21 to 26° C.:

$$C_{end-mid}=0.07282172*(P_{end}^{0.8938195})$$

If T is less than 26 to 33° C.:

$$C_{end-hi}=0.08678193*(P_{end}^{0.8914468})$$

Step 7:
Normalize the pressure reading to a predetermined temperature, e.g., 21° C.

For example:
If T is less than 21° C.:

$$P_{21}=P-(T-21)*C_{lo}$$

If T is between 21 to 26° C.:

$$P_{21}=P-(T-21)*C_{mid}$$

If T is between 26 to 33° C.:

$$P_{21}=P-(T-21)*C_{hi}$$

Step 8:
Normalize the end point pressure to the predetermined temperature (21° C.).

For example:
If T is less than 21° C.:

$$P_{end-21}=P_{end}-(T-21)*C_{end-lo}$$

If T is between 21 to 26° C.:

$$P_{end-21}=P_{end}-(T-21)*C_{end-mid}$$

If T is between 26 to 33° C.:

$$P_{end-21} = P_{end} - (T-21) * C_{end-hi}$$

Step 9:

Determine isotherm equations at the predetermined temperature (21° C.).

For example, for various illustrative gases:

isotherm equations at 21° C.:

$$AsH_3 \text{ Capacity(g/g)}: f(P) = -0.40857 + 0.14009 * (\ln(P+24.5858))$$

$$PH_3 \text{ Capacity(g/g)}: f(P) = -0.29123 + 0.06949 * (\ln(P+73.89104))$$

$$BF_3 \text{ Capacity(g/g)}: f(P) = 0.03949 + 0.00532 * (P^{0.49046})$$

$$GeF_4 \text{ Capacity(g/g)}: f(P) = 0.2394 * (P^{0.2139})$$

$$SiF_4 \text{ Capacity(g/g)}: f(P) = -0.60234 + 0.1223 * (\ln(P+160.6716))$$

wherein g/g is the gram of gas per gram of carbon, and P is the pressure in torr or mmHg.

Step 10:

Determine the amount of gas remaining in the fluid storage and dispensing vessel.

For example:

Weight: Grams of gas remaining in the cylinder (g):

$$G = CW * f(P_{21}) - f(P_{end-21})$$

Volume: Cubic Centimeter of Gas remained in the cylinder (ml):

$$V = (G/MW) * 22400$$

where
- $AsH_3$: MW=78
- $PH_3$: MW=34
- $BF_3$: MW=68
- $GeF_4$: MW=149
- $SiF_4$: MW=104

Cylinder life time: Working hours of the cylinder remaining (hr):

$$HR = (V/sccm)/60$$

wherein sccm is the gas flowrate into the ion source (e.g., 2 ml/min)

The foregoing methodology permits the dynamic monitoring of the gas inventory of the fluid storage and dispensing system in a ready, accurate and reproducible manner, that is outputted by the visual display module in a manner illustrated in FIG. 2 hereof, wherein the vertical height of the fluid column on the visual display is indicative of the amount of fluid remaining in the storage and dispensing vessel of such system.

It will therefore be seen that the system and method of the present invention permit a simple visually perceptible indication of the fluid inventory of vessels in a fluid storage and dispensing system, which is simply and easily applicable to the dynamic monitoring of fluid in supply vessels in a gas box of an ion implanter. The invention overcomes the problems of the prior art including the inability to determine with precision the amount of fluid remaining in vessels for active processing, and the approach to exhaustion of fluid in the fluid supply vessels.

As a result, the system and method of the invention permit the uptime of an ion implanter to be maximized, and the change-out of fluid supply vessels to be accurately predicted and scheduled.

Although the invention has been described herein with reference to illustrative features, aspects and embodiments, it will be appreciated that the invention may be practiced with modifications, variations and in other embodiments, as will suggest themselves to those of ordinary skill based on the disclosure herein. The invention therefore is to be interpreted and construed, as encompassing all such modifications, variations, and other embodiments, within the spirit and scope of the claims hereafter set forth.

What is claimed is:

1. A monitoring system for real-time, continuous monitoring of fluid inventory in an array of fluid-containing vessels in an ion implanter gas box during dispensing of fluid to an ion implanter from on-stream one(s) of said vessels, wherein the fluid-containing vessels include a sorbent medium having sorptive affinity for the fluid and from which the fluid is desorbed under dispensing conditions, said monitoring system comprising:

at least one temperature sensor configured to sense gas box temperature;

at least one pressure sensor configured to continuously sense pressure of fluid within said on-stream one(s) of the vessels or as it leaves said on-stream one(s) of the vessels;

a data acquisition module configured to reside in the gas box, coupled to the at least one temperature sensor and at least one pressure sensor to receive sensing signals from such sensors and to process the signals to generate a corresponding data signal output;

a fiber optic cable configured to be coupled to the data acquisition module in the gas box and to extend through a wall of the gas box and exteriorly of the ion implanter, for transmission of the data signal output of the data acquisition module;

a display arranged for continuously outputting fluid inventory information for said array of said vessels; and a processor coupled to the fiber optic cable exteriorly of the ion implanter to receive the data signal output from the fiber optic cable for the array of said vessels wherein the processor algorithmically determines from said data signal output, using isotherm equations, the amount of fluid remaining in each of the on-stream one(s) of the vessels, and responsively generates on the display a real-time graphical representation of fluid inventory in each of the fluid-containing vessels in the array, wherein said real-time graphical representation comprises a rectangular field and an upper boundary line whose position in the rectangular field indicates fluid inventory of said vessels and wherein the upper boundary line is vertically downwardly translated in the display as the fluid is dispensed from the vessel(s).

2. The monitoring system of claim 1, wherein the processor comprises a data communications interface for downloading of data from the processor.

3. The monitoring system of claim 1, wherein the processor is configured for inputting thereto of an end-point pressure for said dispensing of fluid to the ion implanter from on-stream one(s) of said vessels.

4. The monitoring system of claim 1, wherein the processor is configured to generate a warning output indicative of impending exhaustion of fluid in the on-stream one(s) of said vessels.

5. The monitoring system of claim 1, wherein said system further monitors strain data correlative to strain experienced by the on-stream one(s) of said vessels during fluid dispensing.

6. The monitoring system of claim 1, wherein said system further monitors temperature of the on-stream one(s) of said vessels during fluid dispensing.

7. The monitoring system of claim 1, wherein said system further monitors weight of the on-stream one(s) of said vessels during fluid dispensing.

8. The monitoring system of claim 1, operatively installed in a semiconductor manufacturing facility for monitoring fluid-containing vessels in an ion implanter gas box.

9. The monitoring system of claim 8, wherein the fluid containing vessels in the ion implanter gas box comprise a pressure regulated vessel having a pressure regulator interiorly disposed in the vessel interior volume.

10. The monitoring system of claim 9, wherein the fluid containing vessels contain fluid selected from the group consisting of arsine, phosphine, boron trifluoride, germanium tetrafluoride, and silicon tetrafluoride.

11. The monitoring system of claim 8, wherein the fluid containing vessels in the ion implanter gas box comprise a vessel containing a carbon adsorbent for storing fluid and from which fluid can be desorbed under fluid dispensing conditions.

12. The monitoring system of claim 11, wherein the fluid-containing vessels contain fluid selected from the group consisting of arsine, phosphine, boron trifluoride, germanium tetrafluoride, and silicon tetrafluoride.

13. The monitoring system of claim 1, wherein the system further monitors at least one characteristic, other than fluid temperature and fluid pressure, of fluid supplied by the on-stream one(s) of the fluid-containing vessels.

14. The monitoring system of claim 13, wherein the at least one characteristic of fluid supplied by the on-stream one(s) of the fluid-containing vessels comprises at least one fluid characteristic selected from the group consisting of concentration of one or more components of the fluid, flow rate of the fluid, pressure drop in flow circuitry coupled with on-stream one(s) of the fluid-containing vessels, and cumulative flow rate of the fluid dispensed from the on-stream one(s) of the fluid-containing vessels.

15. A method of real-time, continuous monitoring of fluid inventory in an array of fluid-containing vessels in an ion implanter gas box during dispensing of fluid to an ion implanter from on-stream one(s) of said vessels, comprising use of a monitoring system according to claim 1.

16. The method of claim 15, wherein the system further monitors at least one characteristic, other than fluid temperature and fluid pressure, of fluid supplied by the on-stream one(s) of the fluid-containing vessels.

17. The method of claim 16, wherein the at least one characteristic of fluid supplied by the on-stream one(s) of the fluid-containing vessels comprises at least one fluid characteristic selected from the group consisting of concentration of one or more components of the fluid, flow rate of the fluid, pressure drop in flow circuitry coupled with on-stream one(s) of the fluid-containing vessels, and cumulative flow rate of the fluid dispensed from the on-stream one(s) of the fluid-containing vessels.

* * * * *